(12) United States Patent
Averback et al.

(10) Patent No.: US 6,600,947 B2
(45) Date of Patent: Jul. 29, 2003

(54) METHOD OF DETECTING AMYLOID-CONTAINING LESIONS BY AUTOFLUORESCENCE

(75) Inventors: Paul A. Averback, Beaconsfield (CA); Celine Dupuis, Beaconsfield (CA)

(73) Assignee: Nymox Corporation, St. Laurent (CA)

( * ) Notice: Subject to any disclaimer, the term of this patent is extended or adjusted under 35 U.S.C. 154(b) by 49 days.

(21) Appl. No.: 09/809,137

(22) Filed: Mar. 16, 2001

(65) Prior Publication Data

US 2002/0177778 A1 Nov. 28, 2002

(51) Int. Cl.[7] .................................................. A61B 6/00
(52) U.S. Cl. ....................................... 600/476; 600/407
(58) Field of Search ................................ 600/476, 407; 250/458.1, 459.1, 461.2

(56) References Cited

U.S. PATENT DOCUMENTS

| | | |
|---|---|---|
| 4,816,416 A | 3/1989 | Averback |
| 5,231,170 A | 7/1993 | Averback |
| 5,507,287 A | 4/1996 | Palcic et al. |
| 5,567,720 A | 10/1996 | Averback |
| 5,590,660 A | 1/1997 | MacAulay et al. |
| 5,999,844 A | 12/1999 | Gombrich et al. |
| 6,001,331 A | 12/1999 | Caprathe et al. |
| 6,081,740 A | 6/2000 | Gombrich et al. |
| 6,091,984 A | 7/2000 | Perelman et al. |
| 6,147,800 A | 11/2000 | Faber |

*Primary Examiner*—Marvin M. Lateef
*Assistant Examiner*—Devaang Shah
(74) *Attorney, Agent, or Firm*—Patrick A. Doody; Hunton & Williams (57) ABSTRACT

Disclosed is a method of detecting amyloid-containing deposits in a mammal without administering exogenous chemicals such as fluorophores or chromophores. The method includes subjecting tissue of a mammal, preferably tissue of a mammal suspected of having at least one form of amyloidosis to autofluorescence-initiation, preferably by subjecting the tissue to at least excitation incident radiation from a light source having a wavelength of light within the range of from about 360 to about 370 nm, and more preferably to illumination incident radiation from a light source having wavelengths in the visible spectrum, to produce an emitted light signal beam and a reflected light signal beam. The method also preferably includes detecting the presence of emitted light having a wavelength of from about 400 nm to about 460 nm. The method can be used to diagnose amyloidosis in living mammals using relatively non-invasive imaging apparatus, and it can be used to monitor the efficacy of treatment, or screen effective treatments for amyloidosis.

47 Claims, 3 Drawing Sheets

(2 of 3 Drawing Sheet(s) Filed in Color)

METHOD OF DETECTING AMYLOID-CONTAINING LESIONS BY AUTOFLUORESCENCE

BACKGROUND OF THE INVENTION

1. Field of the Invention

The present invention relates to methods and apparatus for detecting amyloid-containing lesions in tissue using autofluorescence. The invention also relates to methods of detecting the onset of cerebral amyloidosis by detecting the presence of amyloid-containing plaques and other related lesions in brain tissue.

2. Description of Related Art

The term "amyloidosis" encompasses a number of pathological conditions characterized by the deposition of abnormal fibrils ("amyloid fibrils") in extracellular spaces. The amyloid fibril, in turn, represents a final common pathway for a diverse array of proteins. Regardless of their biochemical composition, however, all types of amyloid fibrils share (a) a β-pleated sheet structure, (b) staining similarities, such as green birefringence under polarized light after staining with Congo Red dye, (c) a fibrillar morphology that has a typical electron-microscopic appearance, and (d) other physicochemical properties well known in the art.

The deposition of amyloid fibrils can affect several organs in the systemic forms of the disorder, exemplified by familial Mediterranean fever, familial amyloid polyneuropathy and systemic amyloidosis, or it can be restricted to one organ in localized forms. Among the latter are conditions classified under the rubric "cerebral amyloidosis," which covers the Alzheimer group of diseases, namely, Alzheimer's disease (pre-senile dementia, senile dementia); Alzheimer's disease associated with Down's syndrome; familial Alzheimer's Disease; genetic Alzheimer's disease due to mutations such as Presenilin 1, Presenilin 2, and others; Alzheimer's disease associated with other central-nervous-system diseases, such as Parkinson's disease, Lewy Body Disease, and cerebrovascular diseases; congophilic angiopathy (associated or not associated with Alzheimer's disease, familial or not familial), and other disorders and diseases such as those disclosed in U.S. Pat. No. 6,001,331, the disclosure of which is incorporated by reference herein in its entirety.

Alzheimer's disease (AD) is a complex neurodegenerative disorder characterized by progressive impairments in memory, behavior, language, and visuo-spatial skills, ending ultimately in death. Hallmark pathologies within vulnerable regions include extracellular β-amyloid deposits, intracellular neurofibrillary tangles, synaptic loss, and extensive neuronal cell death. Research on the causes and treatments of Alzheimer's disease has led investigators down numerous avenues. Although many models have been proposed, no single model of AD satisfactorily accounts for all neuropathologic findings as well as the requirement of aging for disease onset, with the exception of that disclosed in Averback, WO 98/34643, the disclosure of which is incorporated by reference herein in its entirety. Considerable evidence has implicated alterations in production or processing of the human amyloid precursor protein (APP) in the etiology of the disease. However, intensive research has proven that AD is a multifactorial disease with many different, perhaps overlapping, etiologies.

Because of this, those in the field have conducted significant research studies and clinical investigations to study the structural deficiencies, chemical changes, and functional abnormalities both within the brain and within different populations of nerve cells. The depth of such investigations and studies are represented by the following publications, which represent only a handful of the vast reports in this arena: *Neurobiology of Alzheimer's Disease* (D. Dawbarn and S. J. Allen, Editors), Bios, Oxford 1995; *Dementia*, (J. Whitehouse, Ed.), F. A. Davis Company, Philadelphia, 1993; *Alzheimer's Disease: Senile Dementia and Related Disorders* (Katzman, R, and R. L. Bick, Eds), Raven Press, New York, 1994, pages 47–51; *Alzheimer's Disease and Related Disorders, Etiology, Pathogenesis and Therapeutics* (Iqbol, K., et al., Eds.), Wiley, Chichester, 1999; *Alzheimer's Disease: Advances in Clinical and Basic Research* (Corain, B, Ed.), Wiley, New York, 1993; *Alzheimer's Disease: Clinical and Treatment Perspectives* (Cutler, N. R., et al., Eds.), Wiley, Chichester, 1995; *Alzheimer's Disease: Therapeutic Strategies* (Giacobini, E., Becker, R., Eds.), Birkhauser, Boston, 1994; Paykel, et al., *Arch. Gen. Psychiat.*, 51:325–332 (1994); Amaducci, et al., *Neurology*, 36:922–931 (1986); McKhann, et al., *Neurology* 34:939–944 (1984), Heston et al., *Arch. Gen. Psychiatry* 38:1085–1090 (1981); *Aging of the Brain* (Gispen and Traber, editors), Elsevier Science Publishers, Amsterdam, 1983, pages 275–282; Heyman et al., *Ann. Neurol* 15:335–341 (1984); Brayne C. and P. Calloway, Lancet 1:1265–1267 (1988); Roth et al., *Br. J. Psychiatry* 149:698–709 (1986); Medical Research Council, *Report from the NRC Alzheimer's Disease Workshop*, London, England, 1987; Morris et al., *Neurology* 41:469–478 (1991); and the references cited within each of these publications.

To date, Alzheimer's disease is the third most expensive disease in the United States, costing society approximately $100 billion each year. It is one of the most prevalent illnesses in the elderly population, and with the aging of society, will become even more significant. Costs associated with AD include direct medical costs such as nursing home care, direct nonmedical costs such as in-home day care, and indirect costs such as lost patient and care giver productivity. Medical treatment and behavior modification may have economic benefits by slowing the rate of cognitive decline, delaying institutionalization, reducing care giver hours, and improving quality of life. Pharmacoeconomic evaluations have shown positive results regarding the effect of drug therapy and behavior modification on nursing home placement, cognition, and care giver time.

Despite the array of research investigations and studies undertaken to date, present clinical evaluations still have a difficult time establishing an unequivocal diagnosis of Alzheimer's Disease. Autopsy or biopsy is widely considered the gold standard method for AD diagnosis. Different criteria exists that assess and determine the presence of neurofibrillary tangles (NFT), cell loss and senile (amyloid) plaques in brain tissue. These criteria for the definite diagnosis of Alzheimer's Disease are met only by histologic evidence.

The research to date has been diverse insofar as the causes of various forms of cerebral amyloidosis. That is, the research has varied with respect to how the actual amyloid plaques and other similar lesions form in the brain. There is little disagreement in the scientific community, however, that a universally accepted indicator of cerebral amyloidosis is the accumulation of large numbers of amyloid-containing lesions, so-called "senile plaques," that are comprised in large part of amyloid fibrils. Senile plaques are spherical, ranging from 10 to 200 μm in diameter, and are found occasionally in aged adult cerebral cortex, but are found in large numbers in Alzheimer-affected cerebral cortex. To date, the best means by which one can measure the presence of senile plaques in the brain is achieved by a brain biopsy or a postmortem examination, and subsequent detection of amyloid plaques.

In this context, various mechanisms have been described by which one can detect amyloid plaques and other amyloid-related lesions. Amyloid plaques and amyloid lesions can be visualized in histological sections by staining with many methods, such as silver impregnation, eosin, periodic acid Schiff, Congo red, thioflavins, and others. Amyloid plaques and amyloid lesions also can be visualized by immunohistochemical methods of staining the amyloid and other proteins in the plaques by antibodies to plaque proteins conjugated to enzymes, such as alkaline phosphatase or horseradish peroxidase and others, or to fluorophores such as fluorescein isothiocyanate, rhodamine, or others.

For example, Dowson reported detection of senile plaques in a post mortem thin slice of brain tissue by fluorescence microscopy. Dowson, J. H., *Histopathology*, 5:305–310 (1981). The thin slices were epi-illuminated with ultraviolet light having a wavelength between 340–380 nm, and the excited light was detected at wavelengths above 430 nm, with the best results around 460 nm. Other means of detecting amyloid plaques have been achieved by staining the thin sections of tissue with a fluorochrome, irradiating the tissue with various wavelengths of light, and detecting the emitted light. Congo Red often is used to stain the thin-section tissue samples to detect the presence of optically anisotropic materials that display congophilic birefringence. This optical phenomenon is recognized as being caused by amyloid plaques and other amyloid-containing components, such as dense microspheres (DMS, or "spherons"). See, U.S. Pat. No. 5,567,720, the disclosure of which is incorporated by reference herein in its entirety.

Methods of staining thin tissue sections are not the same as methods for solving the problems of detecting a signal in whole tissue, and there can be no assurances that a method used on a thin microscopic section can be applied to whole tissue. For example, exogenous chromophores or fluorophores or radiocontrast media, or conjugated fluorophores or chromophores, in vivo usually need to be administered by circulation through the bloodstream, by ingestion by the gastrointestinal route, or by inhalation, etc. Trying to identify particular fluorescence materials in a mass of tissue is complicated further by the number of different tissue fluorophores such as lipofuscin, which autofluoresces yellow and green in a wide range of 400 to 600 nm to excite and 400–640 to detect, and which is ubiquitous in AD brain. Other difficulties encountered in detecting a signal in whole tissue are described in more detail below.

Scientists have attempted to separate amyloid plaque material from postmortem brain by use of fluorescence-activated cell sorting (FACS). Selkoe, et al., have reported a method of purifying amyloid senile plaques from brain tissue by sorting the core plaques using FACS. *J. Neurochem.*, Vol. 46, No. 6, 1820–1834 (1986); and *Methods in Enzymology*, Vol. 134, No. 37, 388–405 (1986). The amyloid plaque cores were detected and separated from the surrounding tissue by using excitation light at 488 nm and emission recognition at 580 nm.

Hanlon reports the ability to distinguish AD brain tissue from non-AD brain tissue using autofluorescence at near infrared wavelengths. Hanlon, et al., *Photochemistry and Photobiology*, 70(2): 236–242 (1999). Hanlon describes exciting tissue samples of AD brain tissue and non-AD brain tissue by irradiating the samples with light at about 647 nm. The samples then are detected with a detection wavelength in the range of from about 665–850 nm. Hanlon reports the ability to distinguish AD brain tissue from non-AD brain tissue using this method, but does not recognize that any signal emanates from amyloid plaques, or that the signal is generated by an amyloid-containing deposit.

All of this research has led down many different paths to the detection of amyloid plaques and other amyloid-related components in thin sections of post mortem brain. There has yet to be developed a relatively non-invasive endogenous method that can be employed without administration of exogenous chromophore of fluorophore by which the specific presence of amyloid plaques, amyloid-containing deposits, and related lesions can be detected in a living animal. This is not surprising given the variety of methods known to detect the presence of amyloid-containing materials in postmortem brain. The various staining techniques with chromophores and fluorophores cannot thus far be used on a living animal, and the autofluorescence techniques to date have suggested a vast array of wavelengths used to test the tissue; Dowson suggesting 340–380 nm for thin-sections of post-mortem brain tissue and 460 nm to detect, Selkoe suggesting 488 nm for FACS of homogenized post-mortem brain tissue, Christie suggesting 720 nm, and Hanlon suggesting the use of near infrared light at 647 nm to excite and 665–850 nm to detect. Trying to identify particular fluorescence materials in a mass of tissue is complicated further by the plethora of divergent tissue fluorophores such as lipofuscin, which autofluoresces yellow and green in a wide range of 400 to 600 nm to excite and 400–640 to detect, and which is ubiquitous in AD brain.

Indeed, the nature of the human brain tissue is such that the use of autofluorescence to detect cell abnormalities produces a large amount of data, most of which is extraneous to the intended measurement. A primary reason for this situation is that tissues contain an extensive and diverse assortment of fluorescent species. Many of the species are present in high concentrations and have excitation bands distributed throughout the ultraviolet and the visible spectra regions.

Another limitation is that the emission band of one fluorophore may overlap the excitation band of another fluorophore, consequently leading to energy transfer between the emission and excitation bands. Consequently, emissions from one fluorophore could possibly excite another fluorophore. The net effect is that exciting a tissue sample at almost any wavelength in the ultraviolet, visible, or infrared wavelength regions causes tissue autofluorescence over a broad spectral range.

It is even more difficult to detect the presence of autofluorescent tissue in the brain because most wavelengths of light will not pass through the skull, and those that do, may cause damage to the tissue. Hanlon discussed above suggests a non-invasive method of diagnosing Alzheimer's Disease using near infrared fluorescent spectroscopy. Backsai, et al., and Skovronsky, et al., disclose imaging techniques such as staining, fluorescent labeling, or radio-labeled ligands that recognize senile plaques that purport to be useful in detecting amyloid plaques in vivo. Injecting or otherwise inserting these compounds into the brain can be problematic given the toxicity and blood-brain barrier concerns.

Recent developments in endoscope technology and fiber optics have led to the production of small and effective imaging and detecting apparatus useful in autofluorescence. For example, U.S. Pat. Nos. 6,147,800, 6,091,984, 6,081,740, 5,507,287, 5,590,660, 5,999,844, and 4,930,516 disclose various apparatus and methods for imaging diseased, often cancerous tissue using autofluorescence. The disclosure of each of these patents is incorporated by reference herein in its entirety. Other autofluorescence apparatus are known in the art (e.g., Pentax SAFE-1000 Autofluorescence-System, available from Pentax-endoscopy.)

The art therefore proposes a number of different approaches to detecting the presence of amyloid plaques and other amyloid-containing lesions, none of which has been proven successful in this regard. While there has yet to be a cure for Alzheimer's Disease, there is effective temporary symptomatic treatment. Diagnosis of AD would be beneficial so that those inflicted therewith could obtain timely treatment to minimize its effects. Diagnosis also is critical for many other reasons such as planning for care, for reducing anxiety when diagnosis is negative, for investigation of putative treatments, and for monitoring therapies.

SUMMARY OF THE INVENTION

There exists a need to develop a method of detecting amyloidosis in the brain and other organs to diagnose conditions involving amyloid-containing deposits and other related lesions such as Alzheimer's disease and other related conditions. There also exists a need to develop a method of detecting amyloidosis in a living animal, preferably without the administration of exogenous chemicals such as fluorophores, chromophores, or antibodies conjugated to fluorphores, chromophores, etc. In addition, there exists a need to develop a system that can detect amyloidosis in the brain and other organs to diagnose conditions involving amyloid-containing deposits.

It is therefore a feature of an embodiment of the invention to provide a method of detecting amyloidosis in the brain and other organs. The method is useful in diagnosing conditions involving amyloid-containing deposits such as Alzheimer's disease and related conditions. It is an additional feature of an embodiment of the invention to provide a system for detecting amyloidosis to diagnose conditions involving amyloid-containing deposits. These and other features of the invention will be readily apparent to those skilled in the art upon reading the description herein.

In accordance with these and other features of the invention, there is provided a method of detecting amyloidosis in a mammal that includes subjecting tissue of a mammal suspected of having at least one form of amyloidosis to autofluorescence-initiation, and detecting the presence of autofluorescence-emitted light having a wavelength of from about 400 nm to about 460 nm.

In accordance with another feature of the invention, there is provided a method of detecting amyloidosis in a mammal that includes subjecting tissue of a mammal suspected of having at least one form of amyloidosis to excitation incident radiation from a light source having a wavelength of light within the range of from about 360 to about 370 nm, and to illumination incident radiation from a light source having wavelengths in the visible spectrum, to produce an emitted light signal beam and a reflected light signal beam, separating the emitted light signal beam from the reflected light signal beam, and detecting the presence of emitted light having a wavelength of from about 400 nm to about 460 nm.

In accordance with an additional feature of an embodiment of the invention, there is provided a method of detecting amyloidosis in a mammal that includes subjecting circulating fluid of a mammal suspected of having at least one form of amyloidosis to excitation incident radiation from a light source having a wavelength of light within the range of from about 360 to about 370 mn, and to illumination incident radiation from a light source having wavelengths in the visible spectrum, to produce an emitted light signal beam and a reflected light signal beam, separating the emitted light signal beam from the reflected light signal beam, and detecting the presence of emitted light having a wavelength of from about 400 nm to about 460 nm.

In accordance with another feature of an embodiment of the invention, there is provided a system for detecting amyloidosis in a mammal that includes a radiation source that illuminates tissue or circulating fluid of a mammal suspected of having at least one form of amyloidosis with: (i) excitation incident radiation having a wavelength of light within the range of from about 360 to about 370 nm; and (ii) illumination incident radiation having wavelengths in the visible spectrum. The system also includes a mechanism for collecting an emitted light signal beam from the tissue or circulating fluid, and a reflected light signal beam from the tissue or circulating fluid, and then separating the emitted light signal beam from the reflected light signal beam. The system further includes a mechanism that is capable of detecting the presence of emitted light having a wavelength of from about 400 nm to about 460 nm.

These and other features of the invention will be readily apparent to those skilled in the art upon reading the detailed description that follows. It should be understood, however, that the detailed description and the specific examples, while indicating preferred embodiments of the invention are given by way of illustration only, since various changes and modifications within the spirit and scope of the invention will become apparent to those skilled in the art from this description. Unless otherwise specified, the respective contents of the documents cited herein are hereby incorporated by reference in their entirety.

BRIEF DESCRIPTION OF THE DRAWINGS

The patent or application file contains at least one drawing executed in color. Copies of this patent or patent application publication with color drawings will be provided by the U.S. Patent and Trademark Office upon request and payment of the necessary fee.

DETAILED DESCRIPTION OF PREFERRED EMBODIMENTS

Throughout this description, the term "amyloidosis" and the expression "cerebral amyloidosis" denotes a number of pathological conditions characterized by the deposition of abnormal fibrils ("amyloid fibrils") and/or related non-fibrillar amyloid precursor or non-precursor molecule, in extracellular spaces, including, for example, the Alzheimer group of diseases, namely, Alzheimer's disease (pre-senile dementia, senile dementia); Alzheimer's disease associated with Down's syndrome; familial Alzheimer's Disease; genetic Alzheimer's disease due to mutations such as Presenilin 1, Presenilin 2, and others; Alzheimer's disease associated with other central-nervous-system diseases, such as Parkinson's disease, Lewy Body Disease, and cerebrovascular diseases; congophilic angiopathy (associated or not associated with Alzheimer's disease, familial or not familial), and other disorders and diseases such as those disclosed in U.S. Pat. No. 6,001,331, the disclosure of which is incorporated by reference herein in its entirety. Throughout this description, the expressions "amyloid plaques" and "amyloid fibrils" denote senile plaques, neuritic plaques, amyloid plaques, amyloid stars, amyloid cores, primitive plaques, classical plaques, burn out plaques, diffuse plaques, shadow plaques, neurofibrillary tangles, amyloid fibrils, paired helical filaments, and the like. Throughout this description, the term "mammal" denotes all mammals, and preferably denotes, sheep, cows, dogs, cats, apes, monkeys, mice, rats, and humans, and most preferably denotes a human.

Throughout this description, the expression "autofluorescence-initiation" denotes any method that is capable of generating an autofluorescence signal from amyloid-containing material, whereby the signal emits light in the wavelength within the range of from about 400 to about 460 nm. Any method capable of generating such a signal is contemplated in the present invention. A particularly preferred method is to subject the tissue to at least excitation incident radiation having a wavelength within the range of from about 360 to about 370 nm. Another preferred method entails subjecting the tissue to the above-described excitation incident radiation, and to illumination incident radiation. Another preferred method entails subjecting the tissue to multi-photon excitation in a multi-photon imaging system, as described in, for example, U.S. Pat. Nos. 6,020,591, 6,166,385, the disclosures of which are incorporated by reference herein in their entirety.

The present inventors have found that amyloid plaque and related lesions ("amyloid") autofluoresce when subjected to certain wavelengths of light. When excited with incident radiation having a wavelength on the order of 360–370 nm amyloid emits a distinct wavelength of detectable radiation within the range of about 400 nm to about 460 nm, and preferably within the range of from about 410 nm to about 440 nm. While not intending on being bound by any theory, it is believed that the radiation emitted by the amyloid is separate and distinct from radiation emitted by other fluorophores typically found at or near amyloid deposits in mammalian brain, (or other circulating tissue or fluids), even those emitting radiation slightly above about 460 nm. This discovery has enabled the inventors to develop a method and system for detecting the presence of amyloid and amyloid-containing lesions, and hence detecting amyloidosis in large three-dimensional tissue samples such as those commonly found in living mammals.

It is preferred in various embodiments of the invention to detect amyloidosis in mammalian brain tissue, nerve tissue, or in circulating fluids that may contain amyloid, such as cerebrospinal fluid, and the like. Preferably, the amyloidosis is detected in mammalian brain tissue. In this context, it is preferred that the method and system be employed to detect amyloidosis in the olfactory bulb or adjacent cerebral cortex, cranial nerve foramina, temporal bones, optic fundus, and mastoid area. It is most preferred to detect amyloidosis in the olfactory bulb, which is part of the first cranial nerve, because this area provides a relatively direct and short access to brain tissue with minimal invasiveness.

The method of the invention encompasses detecting the presence of amyloid-containing deposits by autofluorescence-initiation, and then detecting an autofluorescent signal at a wavelength within the range of from about 400 nm to about 460, nm, preferably from about 410 nm to about 440 nm.

The method of invention preferably entails subjecting tissue or circulating fluid of a mammal suspected of suffering from amyloidosis to excitation incident radiation from a light source having a wavelength of light within the range of from about 360 to about 370 nm. It is preferred to subject the tissue to illumination incident radiation from a light source having a wavelength in the visible spectrum as well. The light source may be varied, such as being comprised of two separate light sources, or one source with a beam splitting mechanism capable of splitting the visible light into two illumination incident radiation light beams, or by filtering one of the illumination incident radiation light beams so that it transmits excitation incident radiation at a wavelength within the range of from about 360 to about 370 nm. Preferably, the excitation incident radiation is at a wavelength of from about 362 to about 368, and most preferably, at about 365 nm. A wider band of excitation incident radiation could be used in the invention, but it is believed that the detection signal will be weaker and/or that certain forms of amyloid or amyloid-containing deposits may go undetected.

In accordance with the present invention, the presence of amyloid-containing deposits is indicated by an autofluorescent signal having a wavelength on the order of about 400 nm to about 460 nm, preferably from about 410 nm to about 440 nm. How that signal is generated is not an essential feature of the present invention. For example, the signal may be generated by using the above-described excitation incident radiation at any suitable wavelength. Alternatively, the signal may be generated by use of a multi-photon excitation using various light or photon sources, such as infrared. The signal also may be generated using various types of light sources, such as a beam of light, a pulse of light or pulsating light, a broadband light source filtered to a specific wavelength, a monochromatic source (e.g., laser), a focused light source, scanning light, and the like. Using the guidelines provided herein, those skilled in the art are capable of designing suitable autofluorescence-initiation methods to generate the signal that indicates the presence of amyloid-containing deposits.

If the tissue or circulating fluid of the mammal contains amyloid-containing deposits, preferably amyloid plaques and related lesions, and most preferably, amyloid plaque, then the amyloid will autofluoresce when subjected to excitation incident radiation at the aforementioned wavelength, or when subjected to other autofluorescence-initiation methods. If the tissue or circulating fluid of the mammal does not contain amyloid, then it will not autofluoresce, or it will autofluoresce to a significantly lesser quantitative degree at a wavelength within the range of from about 400 nm to about 460 nm. It may be possible that tissue other than amyloid that may be present in the mammal autofluoresces at or about the aforementioned wavelengths, but the intensity of the emitted light will be such that it escapes detection or is statistically significantly reduced in quantity with conventional detection apparatus.

The autofluorescence causes amyloid-containing tissue subjected to excitation incident radiation, or to other autofluorescence-initiation methods, to emit radiation in the form of an emitted light signal beam having a wavelength within the range of from about 400 nm to about 460 nm, preferably from about 410 nm to about 440 nm. More preferably, the emitted light signal beam has a wavelength within the range of from about 415 nm to about 430 nm, and most preferably, about 420 nm.

The tissue or circulating fluid subjected to the excitation incident radiation and/or the illumination incident radiation, or to other autofluorescence-initiation methods, also may reflect radiation in the form of a reflected light signal beam. The method of the invention therefore contemplates separating the emitted light signal beam from the reflected light signal beam. This can be accomplished using techniques known in the art and described in, for example, U.S. Pat. Nos. 6,147,800, 6,091,984, 6,081,740, 5,507,287, 5,590,660, and 5,999,844. It is preferred that a light collecting or similar signal detection apparatus be used to collect the emitted light signal beam and the reflected light signal beam prior to passing them to the apparatus used to separate the respective light beams. If only one source of light is used to generated one emission signal, and no reflection signal, then the signal detection apparatus would be suitably designed to only collect the light emitted from the tissue. Those skilled in the art are capable of designing suitable apparatus for collecting and/or splitting various emitted light signal beams and reflected light signal beams, using the guidelines provided herein. It is particularly preferred in the invention to use a dichroic mirror to separate and/or filter the respective light beams.

The method of the invention contemplates detecting the presence of emitted light having a wavelength of from about 400 nm to about 460 nm, thereby indicating the presence of amyloid in the tissue or circulating fluid. This can be accomplished in any number of ways. The separated light signals may be fed to a manipulating and storage device, such as a computer, and ultimately to a video display monitor so that a user can visualize the presence (or absence) of amyloid and make an accurate diagnosis. The size and morphology of the amyloid, if present, also can be determined using the techniques described in, for example, U.S. Pat. No. 6,091,984, the disclosure of which is incorporated by reference herein in its entirety. Skilled artisans are capable of designing suitable manipulation and storage devices for use in the present invention, using the guidelines provided herein.

Figure 1:
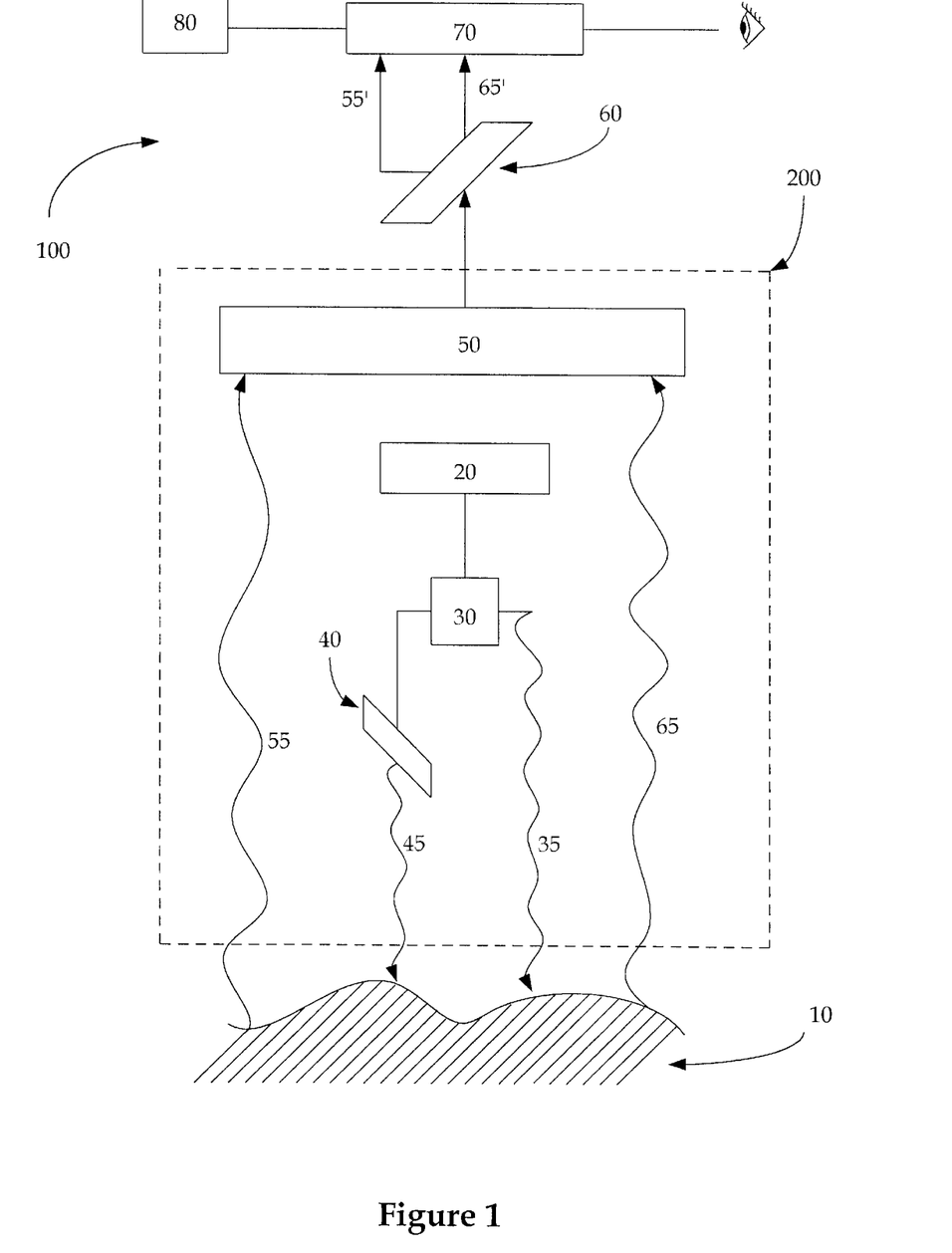
FIG. 1 is a schematic view of a system for detecting amyloidosis in accordance with the present invention.

A system for detecting amyloidosis in a mammal now will be described with reference to FIG. 1. Those skilled in the art will recognize that the system illustrated in FIG. 1 is simplified, and is merely exemplary of the myriad systems that could be used in the present invention. Devices capable of transmitting incident radiation and receiving emitted and reflected radiation are known in the art, and any such device can be used in the present invention. It is preferred that the device be an endoscope equipped with optical fibers. Such devices are disclosed in, for example, U.S. Pat. Nos. 5,199,431 and 5,280,788, the disclosures of which are incorporated by reference in their entirety.

FIG. 1 illustrates a system 100 for imaging tissue 10. It is preferred that the tissue 10 is tissue from a mammalian brain, olfactory bulb, cranial nerve, cerebrospinal fluid, and the like. It will be appreciated that the system 100 can be used to generate a morphological image of amyloid in vivo where use of minimally invasive procedures are advantageous. System 100 utilizes the autofluorescence properties of amyloid in tissues and circulating fluids to discriminate between normal and abnormal tissues and fluids.

The system 100 preferably includes a radiation emitting and collecting system 200, (preferably an endoscope), a light processing unit 60 (preferably a beam splitter, filter such as a dichroic mirror, r a confocal microscopy unit, or a scanner), a computing device 70, and a video monitor 80. The radiation emitting and collecting system 200 preferably is sized and shaped for insertion into the body with minimal invasiveness.

The radiation emitting and collecting system 200 may either be comprised of, or be connected to a radiation source 20. Although FIG. 1 shows radiation source 20 inside system 200, it may be disposed outside, and be operatively connected via optical fibers or cable to system 200, as is well known in the art. FIG. 1 also shows a single radiation source operatively connected to a radiation separator 30, but those skilled in the art will appreciate that two separate radiation sources may be used to produce excitation incident radiation 45, and illumination incident radiation 35, or that only one radiation source 20 may be used to produce only excitation incident radiation 45.

As shown in FIG. 1, system 200 includes a single radiation source 20 operatively connected to a radiation separator 30 by optical cable or fibers, which in turn splits the visible light from radiation source 20 into two illumination incident radiation light beams. One illumination incident radiation light beam 35 is focused on the tissue or circulating fluid being studied. The other illumination incident radiation light beam is filtered with excitation filter 40 so that it transmits an excitation incident radiation light beam 45 at a wavelength preferably within the range of from about 360 to about 370 nm. Those skilled in the art are capable of designing a suitable radiation separator 30 and excitation filter 40, using the guidelines provided herein.

Although FIG. 1 illustrates both an excitation incident radiation light beam 45 and an illumination incident radiation light beam 35, those skilled in the art will appreciate that the invention can be used with any autofluorescence-initiation method. Indeed, a preferred method of the invention involves only the use of excitation incident radiation light beam 45, and it is preferred that the excitation incident radiation light beam 45 be at a wavelength within the range of from about 350 nm to about 380 nm, and more preferably within the range of from about 360 nm to about 370 nm.

Any mechanism known or later discovered that can autofluoresce amyloid-containing lesions in the wavelength of from about 400 nm to about 460 nm can be used in the present invention. For example, dual photon excitation incident radiation can be used instead of one excitation incident radiation light beam 45. In this case, the wavelength of the dual photon, pulsed and focused incident radiation preferably is within the range of from about 700 nm to about 760 nm, and more preferably within the range of from about 720 nm to about 740 nm. Three photon, pulsed, and focused incident radiation also could be used in the present invention, and preferably has a wavelength within the range of from about 1050 nm to about 1140 nm, and more preferably from about 1080 nm to about 1110 nm. Multiphoton incident radiation also can be used within the context of the present invention.

Radiation emitting and collecting system 200 can emit any kind of light and focus the light on the tissue of interest, so long as it causes amyloid-containing deposits to autofluoresce. The system may emit continuous light, or pulsed light, pulsed at any interval, such as every 10 nanoseconds, and the like. The system can emit excitation incident radiation light beam 45 only, or both excitation incident radiation light beam 45 and illumination incident radiation light beam 35. In addition, the light can be a beam of light or a broadband of light that is filtered to the specific wavelengths mentioned above, or the light can be a monochromatic source of light such as a laser.

The radiation emitting and collecting system 200, can accept light from radiation source 20 (internally or externally through fiber optic cable) and transmit both an excitation incident radiation light beam 45 and an illumination incident radiation light beam 35 to tissue or fluid 10 by use of optical fibers or cables. The radiation emitting and collecting system 200 also is capable of collecting both an emitted light signal beam 55 and a reflected light signal beam 65 with a light collection unit 50, which may be disposed within system 200, or be operatively connected to system 200 by optical cables or fibers. The optical fibers present in radiation emitting and collecting system 200 can transmit light in both directions between the distal end (closest to tissue or fluid 10) and the proximal end thereof.

The light emerging from the distal end of radiation emitting and collecting system 200 is reflected by and excites autofluorescence in the tissue or fluid 10. The light reflected by (e.g., reflected light signal beam 65) and the autofluorescent emissions from (e.g., emitted light signal beam 55) the tissue or fluid 10 is collected by the light collection unit 50. Any light collection unit 50 known in the art can be used in the present invention. Suitable light collection units include, but are not limited to, charge coupling devices (CCD) or photo multiplier tubes (PMT).

The light collection unit 50 preferably is operatively connected to light processing unit 60, which is capable of separating light emitted from the tissue or fluid 10, (beam 55), from light reflected by the tissue or fluid 10 (beam 65). Light processing unit 60 can be any light processing unit that is capable of sampling the light and differentiation light have varying wavelengths. Suitable light processing units include, but not limited to, confocal microscopy units, spectral analysis unites, scanning technology, light processing units that are capable of comparing a spectrum of fluorescence from examined tissue to that of known tissue (known normal tissue or known diseased tissue), light processing units capable of processing light over a range of wavelengths (excitation or emission) and subtracting out background light, time-resolved fluorescence detectors, fluorescence polarization detectors, etc.

When time-resolved fluorescence is used, the light collection unit 50 and light processing unit 60 can be designed so that they are capable of being gated to collect and detect fluorescence at varying time intervals. For example, they can be gated for a brief period of, say, 10 nanoseconds, and then opened to detect long fluorescence species. In this context, more than one light collection unit 50 and light processing unit 60 can be used. Here, one can be gated initially and then opened and the other opened and gated making it possible to make a computer-generated image of varying types of fluorophores. Time-resolved fluorescence also enables detection of fluorescence decay over time.

When fluorescence polarization is utilized, those skilled in the art will recognize that the radiation emitting and collecting system 200 will be designed to plane-polarize at least the excitation incident radiation light beam 45. Light collection unit 50 and light processing unit 60 then can be designed to detect the polarization of emitted light from the amyloid-containing species, which depends in part on the movement of the species during the few nanoseconds that pass between absorption of the polarized excitation incident radiation light beam 45 and emission of the emitted light signal beam 55. Larger species move more slowly, and hence, the emitted light signal beam 55 will retain much of the polarization of the polarized excitation incident radiation light beam 45. On the other hand, smaller species move more rapidly thereby depolarizing the fluorescence light when emitted.

Light processing unit 60 also may be a dichroic mirror capable of separating the emitted light signal beam 55 from the reflected light signal beam 65, and thereby generate two separate image streams; reflected image stream 65', and emitted image stream 55'. Skilled artisans are capable of designing a suitable light processing unit 60 capable of generating the respective image streams (whether it be in one unit, two, or more than two units), using the guidelines provided herein.

The reflected image stream 65' and the emitted image stream 55' each is communicated to a computing device 70 for manipulating and storing the images. Preferably, the computing device 70 is in communication with a video monitor 80 wherein the images, either individually or as a composite of a plurality of images can, after the appropriate manipulations, be examined for possible tissue abnormalities. Alternatively, computing device 70 could generate an image to be viewed by the naked eye either through an eyepiece or other suitable viewing device. Skilled artisans are capable of designing a suitable computing device 70 using the guidelines provided herein.

In a combined image, due to the difference in the wavelengths of autofluorescence between normal and abnormal tissues, various regions of the tissue or fluid 10 having abnormalities are visible. The computing device 70 can alternatively perform image processing and image analysis techniques such as edge enhancement and segmentation that can be applied to these images either singly or in combination thereby facilitating abnormality detection and interpretation. Feature recognition permits electronically establishing visual reference points on the examined tissue and relates to the location of features of interest to these reference points. Furthermore, this capability allows joining multiple contiguous fields of view to produce a panoramic display.

Information relating to the state of the tissue or fluid 10 (i.e. normal or abnormal) can be obtained through various methods. For example, in one method of differentiating between normal and abnormal tissues, the intensities of autofluorescence at the selected wavelengths is measured (e.g., between about 400 nm and 460 nm), and the autofluorescence at other wavelengths can be measured. The ratios between the emission intensities for normal and abnormal tissues vary in a characteristic manner. By varying the light transmitted by the radiation source 20 and therefore the excitation wavelengths of excitation incident radiation light beam 45, various other cellular constituents such as porphyrins can be made to autofluorescence in a diagnostically useful manner, and similarly characteristic ratios can be computed. Computing such a ratio on a pixel by pixel basis from a suitably selected pair of images can produce a derived ratiometric image in which the differences between normal and abnormal tissue are accentuated. These derived images may be further processed by methods such as edge enhancement and segmentation to further accentuate any differentiation.

It generally is known that one can differentiate between normal and abnormal tissues or fluids by exciting autofluorescence by illuminating the tissue with light in one wavelength band, measuring the intensity of the light emitted in one or more wavelength bands, computing ratios between those emitted intensities, and discriminating between normality and abnormality on the basis of these ratios. In the present invention, it is preferred to excite autofluorescence by use of excitation incident radiation having a wavelength of from about 360 nm to about 370 nm, and measure the intensity of the emitted light signal beam 55, and the reflected light signal beam 65, whereby the emitted light signal beam 55 has a wavelength within the range of from about 400 nm to about 460 nm.

The method and system of the invention can be used to detect amyloidosis in any tissue in a mammal or fluid where amyloid plaques, amyloid lesions, amyloid-containing deposits, or other similar autofluorescent species exist. For example, the method and system can be used to detect the presence of such autofluorescent species in various organs including the kidney, liver, spleen, lungs, skin, mucosa, ears, eyes, and cerebrospinal fluid.

The method and system of the invention also can be used to monitor treatment and therapy regimens for treating amyloidosis. For example, the method and/or system can be used throughout the course of treatment to determine whether or not the mammal corresponds to the treatment. Over the course of treatment, the mammal will elicit a positive response to the treatment by a weakening in the autofluorescence signals detected in similar areas, or by complete eradication of the signals, or by stabilization of the signals (stopping progression of disease). A negative response to treatment would be indicated by no change or strengthening in the autofluorescence signals detected in similar areas.

In this context, the method and/or system of the invention also is useful in screening suitable therapies, drugs, and other treatment regimens. The method and/or system preferably is used throughout the course of the drug testing, or therapy testing regimen, to determine the efficacy of the therapy, drug, or other treatment regimen.

The method and/or system of the invention also could be used to treat amyloidosis by administering, to a mammal in need thereof, a component that binds to an autofluorescent amyloid plaque or lesion or other similar autofluorescent species, and that alters and/or destroys the plaque, lesion or other species when activated by the excitation incident radiation light beam, or other autofluorescence-initiation method. For example, there are reports of antibodies to amyloid that attack amyloid-beta protein (Wall Street Journal, Mar. 1, 2001) and dissolve the protein material. These antibodies can be designed to recognize and bind to autofluorescent amyloid-containing species in the brain so that when autofluorescence is initiated by any of the above-mentioned methods, the antibodies bind to the amyloid and eradicate it. A component also could be used that is designed to release a chemical or other species that attacks amyloid, whereby the release is triggered by autofluorescence of the amyloid-containing material.

The method and/or system of the invention also can be used to purify amyloid from amyloid-containing tissue. During the purification process, the method and/or system of the invention can be used to detect amyloid-containing materials by autofluorescence. Once detected visually, they can be separated using various visual separation techniques known in the art, such as FACS, and the like.

The method and/or system of the invention also can be used to detect autofluorescence in specified areas of a mammal not heretofore utilized for autofluorescence. Specifically, the method and system can be used to detect autofluorescence in the brain tissue, skin, mucosa, olfactory bulb tissue, cranial nerve foramina, temporal bones, optic fundus, and mastoid areas. The present invention therefore encompasses a method of detecting autofluorescence in any of the aforementioned areas of the body, and preferably, detecting autofluorescence having a wavelength within the range of from about 400 nm to about 460 nm.

Those skilled in the art will recognize that the system of the invention can be modified to accommodate any of aforementioned methods. For example, the system can be modified to incorporate any autofluorescence-initiation method. In this context, the radiation emitting and collecting system 200 can be modified to be any autofluorescence-initiation system, including, for example, multi-photon excitation, and the like. The disclosures of U.S. Pat. Nos. 6,166,385, and 6,020,591, which are incorporated by reference herein in their entirety, disclose various multi-photon autofluorescence-initiation systems that can modified to elicit an autofluorescent signal from amyloid-containing materials in the 400 nm to 460 nm wavelength range. Those skilled in the art are capable of using the systems described in the aforementioned patents in the present invention, using the guidelines provided herein.

In addition, if the system were used to screen effective therapies, and/or to monitor effective treatment regimens, it would include an additional processing unit to collect data over time, and to compare the data with previous data to determine the progression of the autofluorescence signals over time. Such a system also would be useful in detecting autofluorescence whereby a pulse of excitation incident radiation is used, and then autofluorescence is measured over a period of time to determine which species autofluoresce at which time. Again, skilled artisans are capable of adding a suitable processing unit, such as a micro computer or the like, using the guidelines provided herein. Those skilled in the art will appreciate that collecting the data over time, and comparing the data with previous data also can be done manually.

The method and system of embodiments of the present invention are capable of detecting numerous pieces of amyloid-containing material, in addition to amyloid-containing lesions, by using an endogenous procedure. The aforementioned methods described in the literature have detected discrete amyloid lesions by various exogenous techniques, many of which require the use and administration of flurophores, chromophores, staining agents, and the like. The method and system of various embodiments of the invention also are capable of detecting more amyloid-containing material, including more amyloid-containing lesions, than the aforementioned methods described in the literature.

The invention now will be explained in more detail with reference to the following non-limiting examples.

EXAMPLE 1

The brains from 10 cases of sporadic Alzheimer's disease (AD) and 10 age matched normal control cases were examined at postmortem by standard methods to diagnose AD, and to verify the presence of amyloid plaque lesions (SP) in AD, and the absence of SP in the controls. From the brains, blocks were fixed in formalin, embedded in paraffin, cut on a standard microtome, rehydrated, and attached to glass microscope slides using standard techniques. The sections were otherwise untreated.

An Olympus 1×70 inverted microscope with a 100 watt mercury lamp and an Olympus U-MNU filter was used to examine the sections. The filter had an excitation filter of BP 360–370 nm; a barrier filter of BA 420 nm; and a dichroic mirror of DM 400 nm. The appearance, numbers, locations, and signs of signals detected were characterized.

Figure 2:
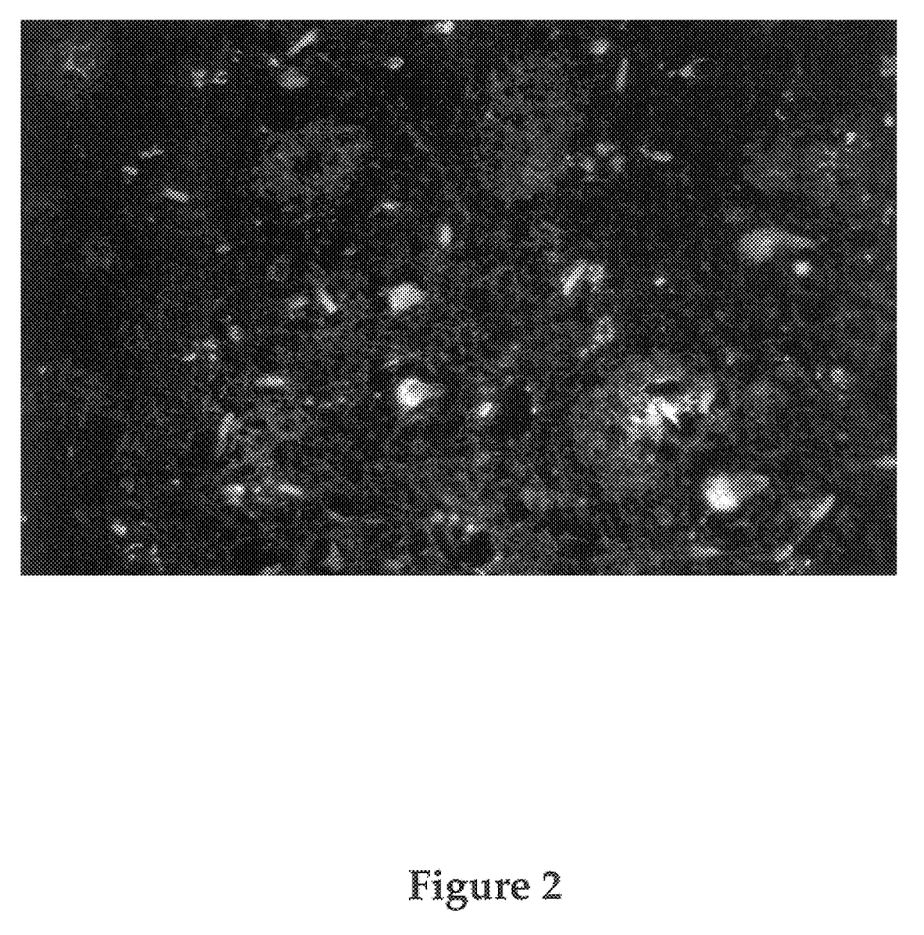
FIG. 2 is a photograph showing autofluorescence of amyloid-containing lesions in a thin slice of tissue, in accordance with Example 1.

FIG. 2 shows amyloid-containing plaques or lesions in a section of AD brain processed in accordance with this example. The plaques are the brightly blue areas of autofluorescence found throughout the photomicrograph. Table 1 summarizes the data from the above cases.

TABLE 1

| Ex. | Number of Cases | Number of blue autofluorescent plaques* |
|---|---|---|
| AD | 10 | 14 ± 3 |
| Controls | 10 | 0 |

*Average number of plaques per medium power field.

Based on the above results, it can be seen that a surprisingly distinctive signal was consistently detected in the AD brain, which was not present, or only minimally present in control brain material. The surprisingly distinctive signal consisted of an endogenous autofluorescent signal, which when generated under the conditions described above, was microscopically predominantly evident as a pale to dark blue emission, having a wavelength within the range of from about 400 nm to about 460 nm, having a round to ovoid shape with a diameter of from about 5 to 150 μm. In other areas, positive signals were present as fine threadlike irregular deposits having a diameter of from about 1–10 μm. Other foci in the brain also gave a pale to dark blue signal, and had other shapes and sizes. These positive signals correlated morphologically with lesions of AD referred to in the literature as senile plaques, neuritic plaques, amyloid plaques, amyloid stars, amyloid cores, primitive plaques, classical plaques, burn out plaques, diffuse plaques, shadow plaques, neurofibrillary tangles, amyloid fibrils, paired helical filaments, and a variety of other terms.

EXAMPLE 2

Microscopic sections from formalin-fixed postmortem brains from six cases of familial AD (FAD), six cases of Down syndrome (trisomy 21) (DS), and six cases of normal controls were examined in accordance with the procedures outlined in Example 1 above. The results are shown in Table 2 below.

TABLE 2

| Ex. | Number of Cases | Number of blue autofluorescent plaques* |
|---|---|---|
| FAD | 6 | 14 ± 4 |
| DS | 6 | 12 ± 4 |
| Controls | 6 | 0 |

*Average number of plaques per medium power field.

From the above table it can be seen that the cases of FAD and DS exhibited strong positive signals that were not present in the controls. The positive signals correlated morphologically with a similar variety of amyloid deposit lesions including diffuse plaques, neuritic plaques, etc., as described above in Example 1.

EXAMPLE 3

Ten random samples of non-amyloidosis, non-AD cases were examined in accordance with the procedures outlined above in Example 1. Tissues were extracted at autopsy and sections made in accordance with Example 1, from the liver, kidney, adrenal, heart, lung, bone marrow, thyroid, parathyroid, spleen, and genitals. The distinctive autofluorescent signal exhibited by the AD tissue in Examples 1 and 2 was not found in any of the normal tissue examined in this example. The distinctive autofluorescent signal also was not seen in random diseased tissue samples which included, inter alia, infectious tissue, infarcts, and tumors. Although a weak positive signal was found in red blood cells, collagen, elastin and other normal tissue elements, this weak signal is easily distinguishable from the strong positive signal generated from the AD tissue in accordance with Examples 1 and 2 above.

EXAMPLE 4

Similar techniques and preparations are used to detect and quantify amyloid and amyloid-like deposits in other tissues such as the skin, kidney, liver, spleen and other organs. In this example, tissue that contains amyloid-containing protein material, or amyloid-containing deposits will emit an autofluorescent signal in the 400 nm to 460 nm wavelength range, whereas tissue that does not contain amyloid-containing protein material, or amyloid-containing deposits will not produce any autofluorescence, or will produce only a weak autofluorescence signal.

EXAMPLE 5

Figure 3:
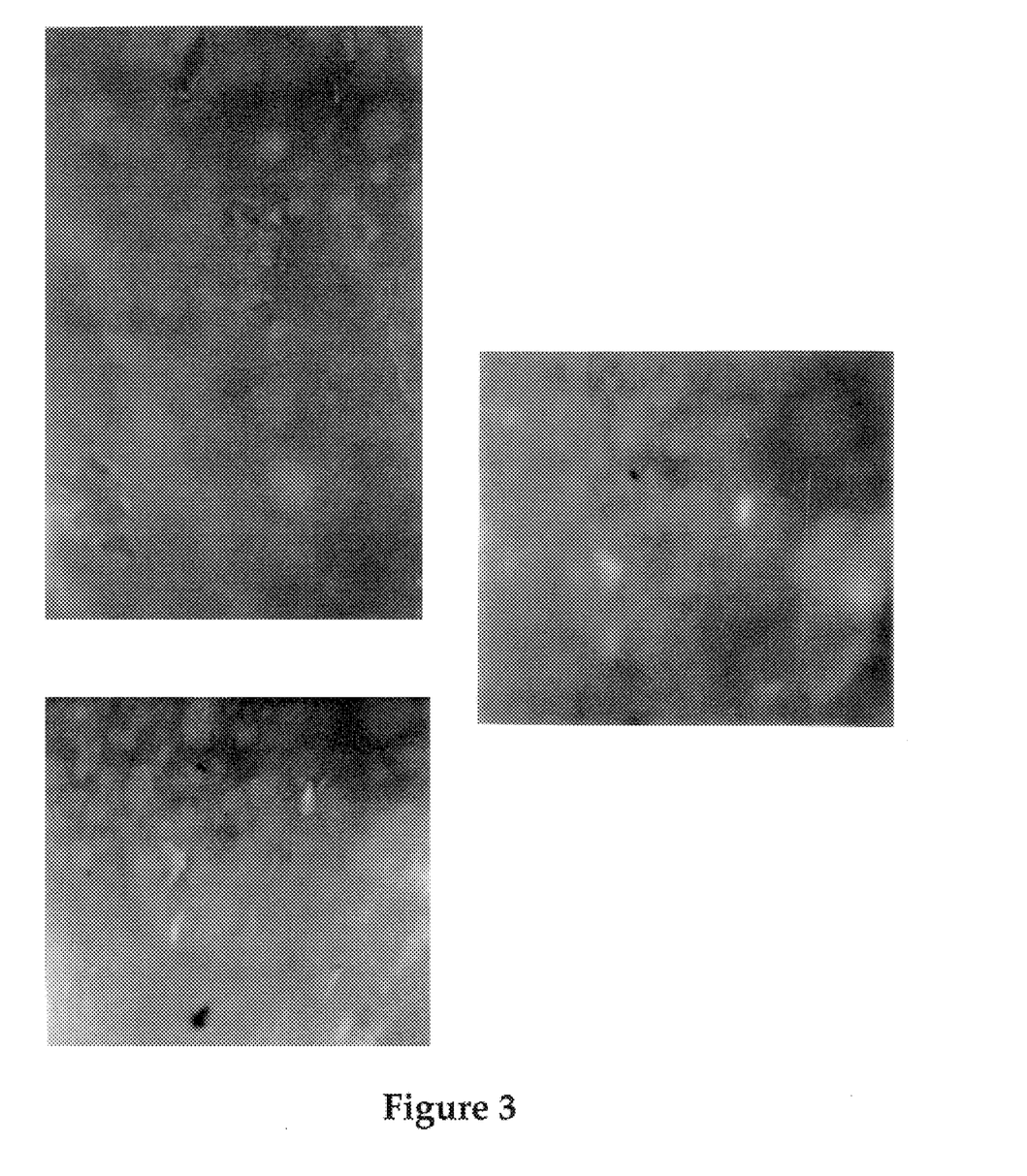
FIG. 3 is a photograph showing autofluorescence of amyloid-containing lesions in three (3) different solid, unsectioned, blocks of tissue in accordance with Example 5.

Solid, unprocessed, and un-sectioned blocks of tissue from Alzheimer's Disease (AD), familial Alzheimer's Disease (FAD), Down's Syndrome (DS), and control subjects, of thicknesses within the range of from about 0.1 to about 0.2 cm, and of a length and width within the range of from about 1 to 3 cm by 1 to 3 cm, were examined directly by the excitation and detection methods described in Example 1 above. The distinctive autofluorescent signal was exhibited by the AD, DS, and FAD blocks of tissues, in a manner similar to that of Examples 1 and 2, whereas no distinctive autofluorescent signal was found in the control subject blocks of tissue. FIG. 3 illustrates three different blocks of tissue showing distinct autofluorescent signals quantitatively indicating the presence of amyloid-containing lesions therein.

EXAMPLE 6

An endoscopic probe, or other radiation emitting and collecting system 200, having sufficient excitation strength and energy, with sufficient detection capacity, and with sufficient flexibility is used to excite and detect autofluorescence signals in living persons. Excitation light having a wavelength within the range of from about 360 nm to about 370 nm is used to detect and quantify amyloidosis, (by detecting amyloid plaques and amyloid-like lesions) by detecting autofluorescent signals from individuals suspected of having AD or at risk for developing AD, or suspected of having amyloid types of disease or at risk of developing other amyloid types of disease, or suspected of having or being at risk for diseases with positive signals produced by endogenous autofluorescent lesions excited by the above-mentioned excitation light. The probe is used on the skin to detect autofluorescent skin signals, on mucosa to detect autofluorescent mucosal signals, on the eye and ear to detect eye and ear signals, and on other organs to detect their signals.

A similar probe is introduced internally into body cavities, blood vessels, orifices and other non-superficial body locations of the class of individuals described above. The distinctive autofluorescent signal produced by the amyloid lesions and deposits described above in Examples 1 and 2 is detected.

EXAMPLE 7

An endoscopic probe, or other radiation emitting and collecting system 200, having sufficient excitation strength and energy, with sufficient detection capacity, and with sufficient flexibility is introduced into areas of non-nervous tissue where there is sufficient proximity to the nervous tissues known to contain amyloid plaques or amyloid lesions such that the autofluorescent signals described in Examples 1 and 2 above can be detected outside the nervous tissue. Specifically, the probe or system described above in this example is directed into the nasal cavity approaching the lamina cribosa (a bone in the skull behind the nasal bones) to detect autofluorescent signals from the olfactory bulb, (a part of the first cranial nerve which is known to contain SP in AD), or adjacent cerebral cortex. The system detects individuals suffering from amyloidosis and differentiates them from individuals who are not suffering from amyloidosis.

In a similar fashion, the probe or system described above in this example is utilized to detect the autofluorescent signals from cranial nerve foramina, temporal bones, optic fundus, mastoid area, and other locations.

While the invention has been described in detail with reference to particularly preferred embodiments and examples, those skilled in the art will appreciate that various modifications may be made to the invention without departing from the spirit and scope thereof.

What is claimed is:

1. A method of detecting amyloidosis comprising:
   subjecting tissue of a mammal suspected of having at least one form of amyloidosis to autofluorescence-initiation; and
   detecting amyloidosis by detecting the presence of emitted light having a wavelength of from about 400 nm to about 460 nm.

2. The method as claimed in claim 1, wherein the autofluorescence-initiation comprises:
   subjecting the tissue to excitation incident radiation from a light source having a wavelength of light within the range of from about 360 to about 370 nm, and to illumination incident radiation from a light source having wavelengths in the visible spectrum, thereby generating an emitted light signal beam and a reflected light signal beam.

3. The method as claimed in claim 1, wherein the mammal is a living mammal.

4. The method as claimed in claim 1, wherein the living mammal is a human being.

5. The method as claimed in claim 1, wherein the tissue is selected from the group consisting of brain tissue, skin, mucosa, olfactory bulb tissue, cranial nerve foramina, temporal bones, optic fundus, and mastoid areas.

6. The method as claimed in claim 4, wherein the brain tissue is cerebral cortex tissue.

7. The method as claimed in claim 1, wherein the method detects the presence of emitted light having a wavelength of from about 410 nm to about 440 nm.

8. The method as claimed in claim 7, wherein the method detects the presence of emitted light having a wavelength of about 420 nm.

9. The method as claimed in claim 2, further comprising separating the emitted light signal beam from the reflected light signal beam, wherein separating the emitted light signal beam from the reflected light signal beam comprises:
   collecting the emitted light signal beam and the reflected light signal beam; and
   passing the collected light signal beams through a light processing unit.

10. The method as claimed in claim 9, wherein the light processing unit is selected from the group consisting of confocal microscopy, a scanning apparatus, a dichroic mirror, a time-resolved fluorescence processing unit, and a fluorescence polarization processing unit.

11. A method of detecting amyloidosis comprising:
    subjecting fluid of a mammal suspected of having at least one form of amyloidosis to autofluorescence-initiation; and
    detecting amyloidosis by detecting the presence of emitted light having a wavelength of from about 400 nm to about 460 nm.

12. The method as claimed in claim 11, wherein the autofluorescence-initiation comprises:
    subjecting the fluid to excitation incident radiation from a light source having a wavelength of light within the range of from about 360 to about 370 nm, and to illumination incident radiation from a light source having wavelengths in the visible spectrum, thereby generating an emitted light signal beam and a reflected light signal beam.

13. The method as claimed in claim 11, wherein the mammal is a living mammal.

14. The method as claimed in claim 11, wherein the living mammal is a human being.

15. The method as claimed in claim 11, wherein the fluid is selected from the group consisting of blood, urine, cerebrospinal fluid, saliva, sweat, and tears.

16. The method as claimed in claim 15, wherein the fluid is cerebrospinal fluid.

17. The method as claimed in claim 11, wherein the method detects the presence of emitted light having a wavelength of from about 410 nm to about 440 nm.

18. The method as claimed in claim 17, wherein the method detects the presence of emitted light having a wavelength of about 420 nm.

19. The method as claimed in claim 12, further comprising separating the emitted light signal beam from the reflected light signal beam, wherein separating the emitted light signal beam from the reflected light signal beam comprises:
    collecting the emitted light signal beam and the reflected light signal beam; and
    passing the collected light signal beams through a light processing unit.

20. The method as claimed in claim 18, wherein the light processing unit is selected from the group consisting of confocal microscopy, a scanning apparatus, a dichroic mirror, a time-resolved fluorescence processing unit, and a fluorescence polarization processing unit.

21. A system for detecting amyloidosis in a mammal, comprising:
    (a) a radiation source capable of subjecting tissue or circulating fluid of a mammal suspected of having at least one form of amyloidosis with: (i) excitation incident radiation having a wavelength of light within the range of from about 360 to about 370 nm; and optionally with (ii) illumination incident radiation having wavelengths in the visible spectrum;
    (b) a mechanism for collecting an emitted light signal beam from the tissue or circulating fluid, and optionally a reflected light signal beam from the tissue or circulating fluid;
    (c) a mechanism for processing the collected light signal beams to generate at least an excited image stream;
    (d) a mechanism that is capable of detecting the presence of emitted light having a wavelength of from about 400 nm to about 460 nm from the excited image stream.

22. The system as claimed in claim 21, wherein the mechanism for processing the collected light signal beams to generate at least an excited image stream comprises one or more mechanisms selected from the group consisting of confocal microscopy, a scanning apparatus, a dichroic mirror, a time-resolved fluorescence processing unit, and a fluorescence polarization processing unit.

23. The system as claimed in claim 21, wherein the mechanism capable of detecting the presence of emitted light having a wavelength of from about 400 nm to about 460 nm comprises a computing device and a video monitor.

24. A method of monitoring treatment of amyloidosis comprising:

repeating the method as claimed in claim 1 on a mammal undergoing treatment of amyloidosis over a period of time in which the mammal is undergoing the treatment;

collecting and storing the quantity and strength of emitted light having a wavelength of from about 400 nm to about 460 nm over a period of time in which the mammal is undergoing the treatment; and comparing the quantity and strength of emitted light having a wavelength of from about 400 nm to about 460 nm over time to determine whether the quantity and/or strength of the emitted light has changed.

25. The method as claimed in claim 24, wherein the mammal is a human being.

26. The method as claimed in claim 24, wherein the tissue is selected from the group consisting of brain tissue, skin, mucosa, olfactory bulb tissue, cranial nerve foramina, temporal bones, optic fundus, and mastoid areas.

27. The method as claimed in claim 26, wherein the brain tissue is cerebral cortex tissue.

28. The method as claimed in claim 24, wherein the method detects the presence of emitted light having a wavelength of from about 410 nm to about 440 nm.

29. A method of screening potential treatments of amyloidosis comprising:

subjecting a mammal to a potential treatment for amyloidosis;

repeating the method as claimed in claim 1 on the mammal undergoing potential treatment for amyloidosis over a period of time in which the mammal is undergoing the potential treatment;

collecting and storing the quantity and strength of emitted light having a wavelength of from about 400 nm to about 460 nm over a period of time in which the mammal is undergoing the potential treatment; and comparing the quantity and strength of emitted light having a wavelength of from about 400 nm to about 460 nm over time to determine whether the quantity and/or strength of the emitted light has changed.

30. The method as claimed in claim 29, wherein subjecting the mammal to the potential treatment comprises administration of potential drugs suspected of being useful in treating amyloidosis.

31. The method as claimed in claim 29, wherein the tissue is selected from the group consisting of brain tissue, skin, mucosa, olfactory bulb tissue, cranial nerve foramina, temporal bones, optic fundus, and mastoid areas.

32. The method as claimed in claim 31, wherein the brain tissue is cerebral cortex tissue.

33. The method as claimed in claim 29, wherein the method detects the presence of emitted light having a wavelength of from about 410 nm to about 440 nm.

34. A method of detecting amyloidosis comprising:

subjecting tissue of a mammal suspected of having at least one form of amyloidosis to excitation incident radiation from a light source having a wavelength of light within the range of from about 360 to about 370 nm, and to illumination incident radiation from a light source having wavelengths in the visible spectrum, thereby generating an emitted light signal beam and a reflected light signal beam;

separating the emitted light signal beam from the reflected light signal beam; and detecting amyloidosis by detecting the presence of emitted light having a wavelength of from about 400 nm to about 460 nm.

35. The method as claimed in claim 34, wherein the mammal is a human being.

36. The method as claimed in claim 34, wherein the tissue is selected from the group consisting of brain tissue, skin, mucosa, olfactory bulb tissue, cranial nerve foramina, temporal bones, optic fundus, and mastoid areas.

37. The method as claimed in claim 36, wherein the brain tissue is cerebral cortex tissue.

38. The method as claimed in claim 34, wherein the method detects the presence of emitted light having a wavelength of from about 410 nm to about 440 nm.

39. A method of detecting amyloidosis comprising:

subjecting tissue of a mammal suspected of having at least one form of amyloidosis to autofluorescence-initiation, whereby the tissue is selected from the group consisting of brain tissue, skin, mucosa, olfactory bulb tissue, cranial nerve foramina, temporal bones, optic fundus, and mastoid areas; and detecting amyloidosis by detecting the presence of emitted light having a wavelength of from about 400 nm to about 460 nm.

40. The method as claimed in claim 39, wherein the mammal is a human being.

41. The method as claimed in claim 39, wherein the method detects the presence of emitted light having a wavelength of from about 410 nm to about 440 nm.

42. The method as claimed in claim 39, wherein the brain tissue is cerebral cortex tissue.

43. A method of treating amyloidosis comprising:

administering, to a mammal in need thereof, a component that binds to an autofluorescent amyloid-containing lesion, and that alters and/or destroys the amyloid material present in the amyloid-containing lesion;

carrying out the method recited in claim 1; and detecting a reduction in the amount of material that emits light having a wavelength of from about 400 to about 460 nm.

44. A method of detecting autofluorescence comprising:

subjecting tissue to autofluorescence-initiation, the tissue being selected from the group consisting of brain tissue, skin, mucosa, olfactory bulb tissue, cranial nerve foramina, temporal bones, optic fundus, and mastoid areas; and detecting amyloidosis by detecting the presence of autofluorescence light.

45. The method as claimed in claim 44, wherein the tissue is olfactory bulb tissue.

46. The method as claimed in claim 44, wherein detecting the presence of autofluorescence light comprises detecting the presence of light having a wavelength within the range of from about 400 nm to about 460 nm.

47. The method as claimed in claim 46, wherein the light has a wavelength within the range of from about 410 nm to about 440 nm.

* * * * *